United States Patent [19]
Avila et al.

[11] Patent Number: 6,102,861
[45] Date of Patent: Aug. 15, 2000

[54] METHOD AND APPARATUS FOR THREE-DIMENSIONAL ULTRASOUND IMAGING USING SURFACE-ENHANCED VOLUME RENDERING

[75] Inventors: Ricardo Scott Avila; Lisa Sobierajski Avila, both of Clifton Park, N.Y.; Brian Peter Geiser, Hartland, Wis.; William Thomas Hatfield, Schenectady, N.Y.; Vaishali Vilas Kamat, Waukesha; Todd Michael Tillman, West Milwaukee, both of Wis.

[73] Assignee: General Electric Company, Schenectady, N.Y.

[21] Appl. No.: 09/299,031

[22] Filed: Apr. 23, 1999

[51] Int. Cl.$^7$ ............................................ A61B 8/00
[52] U.S. Cl. .................................. 600/443; 128/916
[58] Field of Search .................... 600/443, 447, 600/437, 441; 128/916; 73/626; 382/274

[56] References Cited

U.S. PATENT DOCUMENTS

| | | | |
|---|---|---|---|
| 5,706,816 | 1/1998 | Mochizuki et al. | 128/660.07 |
| 5,899,863 | 5/1999 | Hatfield et al. | 600/443 |
| 5,954,653 | 9/1999 | Hatfield et al. | 600/443 |
| 6,019,725 | 2/2000 | Vesely et al. | 600/447 |

*Primary Examiner*—Marvin M. Lateef
*Assistant Examiner*—Ali M. Imam
*Attorney, Agent, or Firm*—Marvin Snyder; Douglas E. Stoner

[57] ABSTRACT

In performing for three-dimensional ultrasound imaging of an object from any angle relative to the plane of acquisition, a human body is scanned to acquire multiple images forming a data volume. The system computer generates a multiplicity of reformatted slices through the data volume and parallel to the imaging plane. For each projected pixel, a ray is cast through the reformatted slices onto the imaging plane. For each pixel along the ray, the accumulated intensity is calculated as a function of the pixel and opacity values for the pixel being processed, the accumulated intensity calculated at the preceding pixel the remaining opacity for the subsequent pixels. The final accumulated intensity for each ray is obtained when the remaining opacity reaches a predetermined minimum. The accumulated intensities for all cast rays form the projected image.

20 Claims, 5 Drawing Sheets

METHOD AND APPARATUS FOR THREE-DIMENSIONAL ULTRASOUND IMAGING USING SURFACE-ENHANCED VOLUME RENDERING

FIELD OF THE INVENTION

This invention generally relates to three-dimensional ultrasound imaging of the human anatomy for the purpose of medical diagnosis. In particular, the invention relates to methods and apparatus for three-dimensional imaging of the human anatomy by detecting ultrasonic echoes reflected from a scanned volume in a human body.

BACKGROUND OF THE INVENTION

Conventional ultrasound scanners create two-dimensional B-mode images of tissue in which the brightness of a pixel is based on intensity of the echo return. Alternatively, in a color flow imaging mode, movement of fluid (e.g., blood) or tissue can be imaged. Measurement of blood flow in the heart and vessels using the Doppler effect is well known. The phase shift of backscattered ultrasound waves may be used to measure velocity of the backscatterers from tissue or blood. The Doppler shift may be displayed using different colors to represent speed and direction of flow. In power Doppler imaging, the returned Doppler signal power is displayed. Although the following discussion refers predominantly to B-mode imaging for the sake of brevity, the present invention applies to any mode of ultrasound imaging.

Two-dimensional ultrasound images are often difficult to interpret due to inability of the observer to visualize the two-dimensional representation of the anatomy being scanned. In addition, it may not be possible to acquire the precise view needed to make a diagnosis due to probe geometry or poor access to the area of interest. However, if the ultrasound probe is swept over an area of interest and two-dimensional images are accumulated to form a three-dimensional data volume, the anatomy becomes much easier to visualize for both the trained and untrained observer. Also, views which cannot be acquired due to probe geometry or poor access to the area of interest can be reconstructed from the three-dimensional data volume by constructing slices through the volume at the angle that is otherwise difficult to obtain.

In order to generate three-dimensional images, the imaging system computer can transform a source data volume retrieved from memory into an imaging plane data set. The successive transformations may involve a variety of projection techniques such as maximum, minimum, composite, surface or averaged projections made at angular increments, e.g., at 10° intervals, within a range of angles, e.g., +90° to −90°. Each pixel in the projected image includes the transformed data derived by projection onto a given image plane.

In free-hand three-dimensional ultrasound scans, a transducer array (1D to 1.5D) is translated in the elevation direction to acquire a set of image planes through the anatomy of interest. These images can be stored in memory and later retrieved by the system computer for three-dimensional reconstruction. If the spacings between image frames are known, then the three-dimensional volume can be reconstructed with the correct aspect ratio between the out-of-plane and scan plane dimensions. If, however, the estimates of the inter-slice spacing are poor, significant geometric distortion of the three-dimensional object can result.

A conventional ultrasound imaging system collects B-mode, color flow mode and power Doppler mode data in a cine memory on a continuous basis. As the probe is swept over an area of the anatomy, using either a free-hand scanning technique or a mechanical probe mover, a three-dimensional volume is stored in the cine memory. The distance the probe was translated may be determined by any one of a number of techniques. The user can provide an estimate of the distance swept. Alternatively, if the probe is moved at a constant rate by a probe mover, the distance can easily be determined. Attachment of a position sensor to the probe to determine the position of each slice os amptjer a;termatove/. Markers on the anatomy or within the data could also provide the required position information. Yet another technique is to estimate the scan plane displacements directly from the degree of speckle decorrelation between successive image frames. Once the data volume has been acquired, the central processing unit can provide three-dimensional projections of the data as well as arbitrary slices through the data volume.

It is often desirable to form a three-dimensional projection of the surface of an internal structure during diagnostic medical imaging. For instance, in obstetrics, it is often desirable to scan parts of the fetal anatomy (hands, feet, or face) to look for possible fetal defects. Techniques have been developed which produce a single three-dimensional projection of fetal anatomy from a fixed position. These techniques require that the baby's face be oriented so that it is looking up at the transducer and most often use special positioning devices such as a motorized probe mover. A range gate is often used to eliminate unwanted anatomy from the data volume to be rendered. In addition, simplifying assumptions are made in the compositing algorithm to speed up rendering. While this technique appears to produce reasonable results, it has several drawbacks.

In practice, it is unrealistic to require that the baby being imaged be in a fixed orientation, so any technique with this requirement will have limited application. Further, a single view is often not enough to make a definitive diagnosis of a defect. Thus there is a need for a technique which does not require either a special probe or that the object being imaged be in any particular orientation and which allows the object to be viewed from any angle.

SUMMARY OF THE INVENTION

Three-dimensional imaging of an object from any angle relative to the plane of acquisition is accomplished in an ultrasound imaging system which scans a human body and collects multiple images (e.g., B mode) in a cine memory to form a data volume. The system computer then performs a surface-enhanced volume rendering.

In accordance with a preferred embodiment of the invention, the system computer generates an opacity function. The opacity varies from zero to unity as a function of the pixel value. Then the system computer generates a multiplicity of reformatted slices through the data volume and parallel to the imaging plane. For each projected pixel, a ray is cast through the reformatted slices onto the imaging plane. For each pixel along the ray, the accumulated intensity is calculated as a function of the pixel and opacity values for the pixel being processed, the accumulated intensity calculated at the preceding pixel, and the remaining opacity for the subsequent pixels. The final accumulated intensity for each ray is obtained when the remaining opacity reaches a predetermined minimum. The accumulated intensities for all cast rays form the projected image, which is stored in cine memory and then selectively displayed. Optionally, the projected image may be scaled and subjected to contrast enhancement prior to storage in the cine memory.

DETAILED DESCRIPTION OF THE PREFERRED EMBODIMENTS

Figure 1:
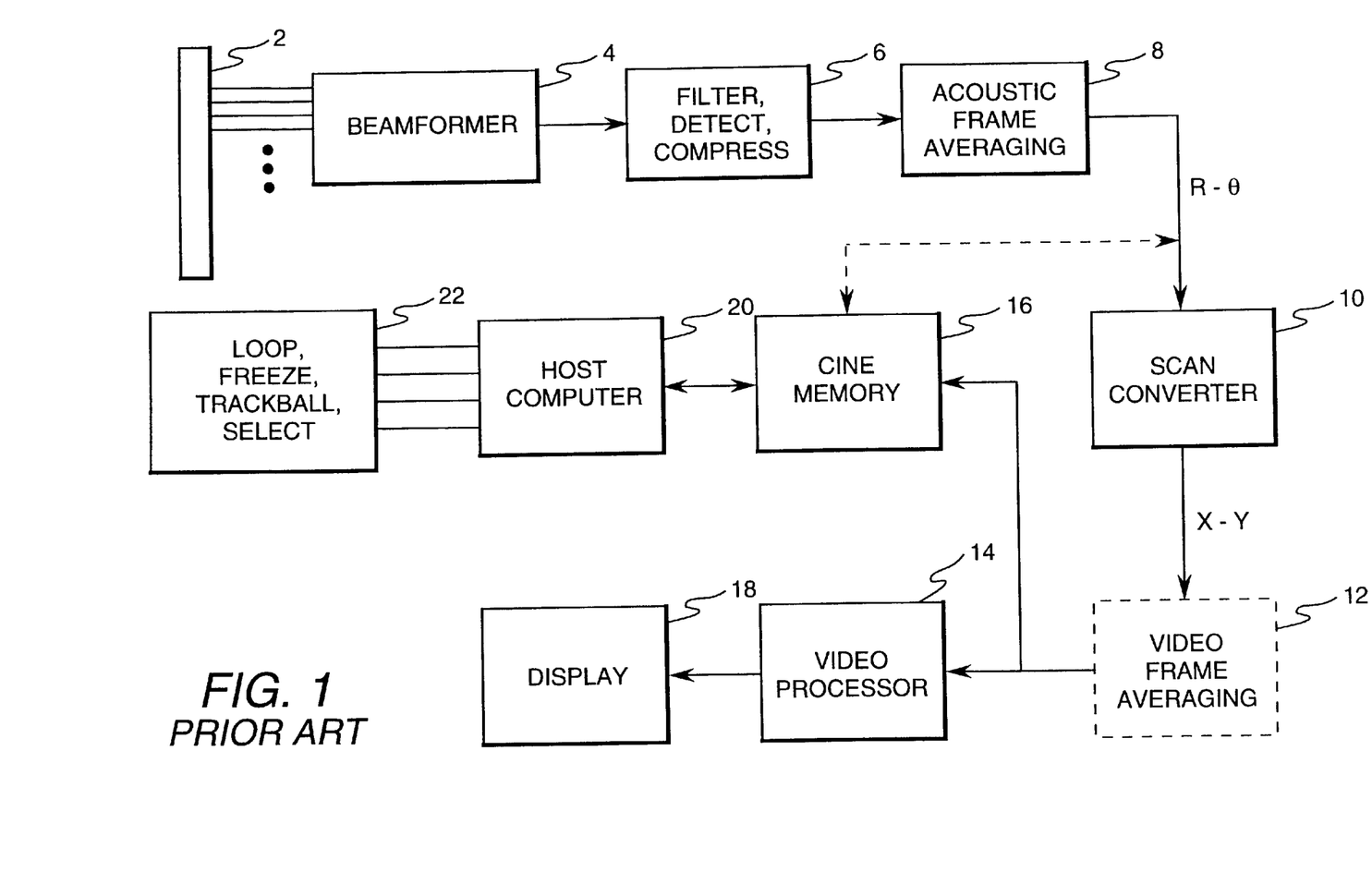
FIG. 1 is a block diagram generally depicting various subsystems of a conventional real-time digital ultrasound imaging system.

The basic signal processing chain in the conventional B-mode imaging system is depicted in FIG. 1. An ultrasound transducer array 2 is activated to transmit an ultrasound beam focused at a transmit focal position. The return RF signals are detected by the transducer elements and then dynamically focused at successive ranges along a scan line by a beamformer 4 to form a receive vector. The beamformer output data (I/Q or RF) for each scan line is passed through a B-mode processing chain 6 which includes equalization filtering, envelope detection and logarithmic compression. Depending on the scan geometry, up to a few hundred vectors may be used to form a single acoustic image frame. To smooth the temporal transition from one acoustic frame to the next, some acoustic frame averaging 8 may be performed before scan conversion. For a sector scan, compressed images in R-θ format are converted by a scan converter 10 into X-Y format for display. On some systems, frame averaging may be performed on the X-Y data (indicated by dashed block 12) rather than the acoustic frames before scan conversion, and sometimes duplicate video frames may be inserted between acoustic frames in order to achieve a given video display frame rate. The scan-converted frames are passed to a video processor 14, which basically maps the scan-converted data to a display gray or color map for video display.

System control is centered in a host computer 20, which accepts operator inputs through an operator interface 22 and in turn controls the various subsystems. (In FIG. 1, the system control lines from the host computer to the various subsystems have been omitted for the sake of simplicity.) During imaging, a long sequence of the most recent images is stored and continuously updated automatically in a cine memory 16. Some systems are designed to save the R-θ acoustic images (this data path is indicated by the dashed line in FIG. 1), while other systems store the X-Y video images. The image loop stored in cine memory 16 can be reviewed on the display monitor via trackball control (interface 22), and a section of the image loop can be selected for hard disk storage.

For an ultrasound scanner with free-hand three-dimensional imaging capability, the selected image sequence stored in cine memory 16 is transferred to host computer 20 for three-dimensional reconstruction. The result is written back into another portion of the cine memory or to scan converter memory, from where it is sent to the display system 18 via the video processor 14.

Figure 2:
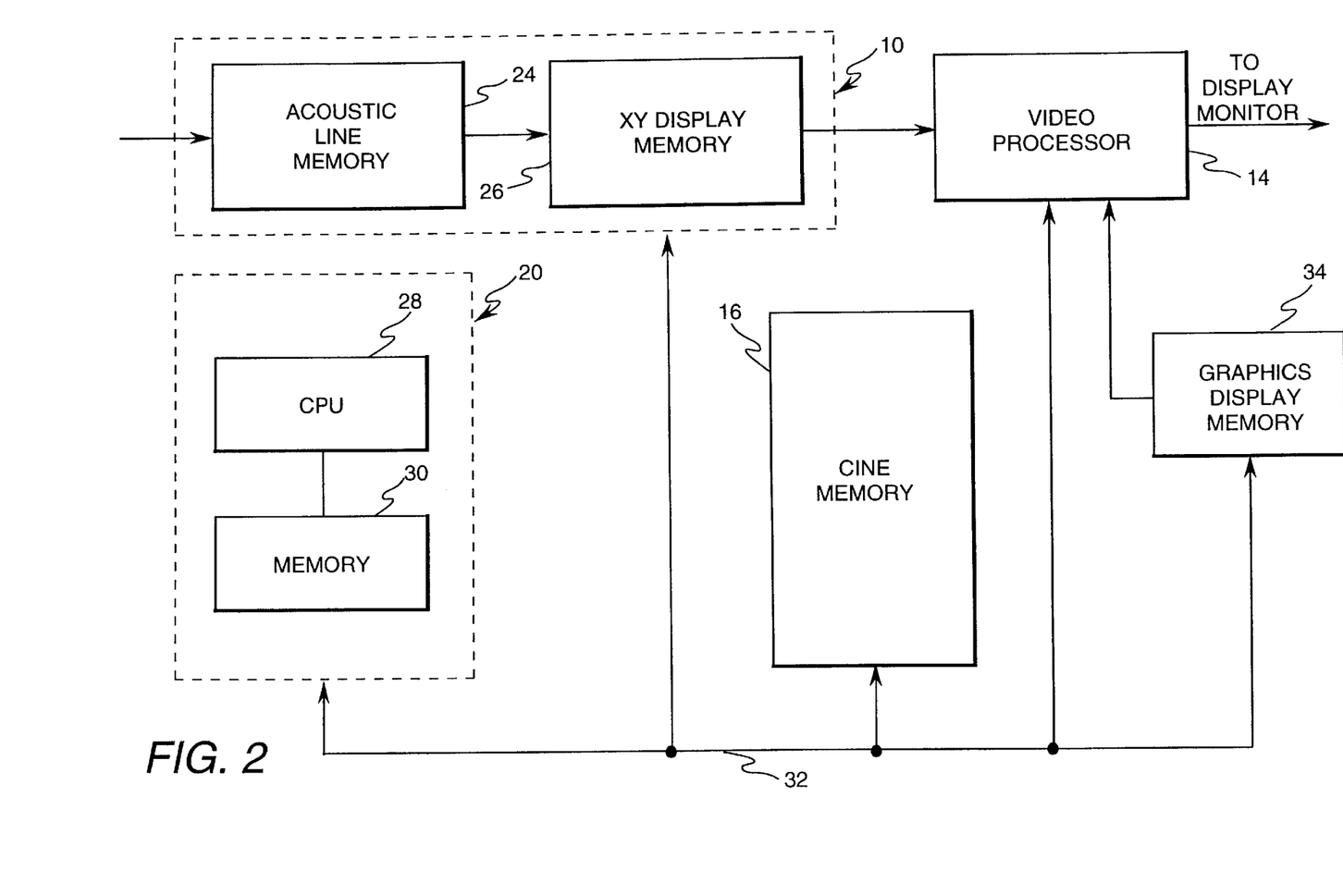
FIG. 2 is a block diagram showing the means for reconstructing frames comprising successive volumetric projections of pixel data in accordance with a preferred embodiment of the invention.

Referring to FIG. 2, scan converter 10 comprises an acoustic line memory 24 and an XY display memory 26. The B-mode imaging data stored in polar coordinate (R-θ) sector format in acoustic line memory 24 are transformed to appropriately scaled Cartesian coordinate intensity data, which are stored in XY display memory 26. Each image frame out of XY display memory 26 is sent to video processor 14. Before gray mapping, frames of B-mode imaging data in the video processor 14 are stored in cine memory 16 on a first-in, first-out basis. Storage can be continuous or as a result of an external trigger event. The cine memory 16 is like a circular image buffer that runs in the background, capturing image data that are displayed in real time to the user. When the user freezes the system (by operation of an appropriate device on operator interface 22), the user has the capability to view image data previously captured in cine memory.

The selected image sequence stored in cine memory 16 is transferred to host computer 20 for three-dimensional reconstruction. The multiple frames of imaging data acquired during the sweep of the probe form a three-dimensional data volume. Host computer 20 retrieves the region of interest from cine memory 16 and uses a volume rendering technique to reconstruct projected images onto various imaging planes. The projected data resulting from each projection are written back into another portion of the cine memory or to scan converter memory, from where they are sent to display monitor 18 via video processor 14.

Host computer 20 comprises a central processing unit (CPU) 28 and system memory 30. CPU 28 is programmed to transform an acquired volume of imaging data into a multiplicity of three-dimensional projection images taken at different angles. CPU 28 controls the flow of data between X-Y display memory 26, video processor 14, cine memory 16 and the CPU itself via the system control bus 32. Each frame of imaging data, representing one of a multiplicity of scans or slices through the object being examined, is stored sequentially in acoustic line memory 24, in x-Y memory 26 and in video processor 14. Before gray mapping, frames of B-mode imaging data are sent from the video processor to cine memory 16. A stack of frames, representing the scanned object volume, is stored in cine memory 16, forming a source data volume. Once the source data volume has been acquired, CPU 28 can provide three-dimensional projections of the data as well as arbitrary slices through the source data volume.

The conventional system has the capability to superimpose graphical symbols on any ultrasound image. The superimposition of graphics on the image frame is accomplished in the video processor 14, which receives the ultrasound image frame from XY display memory 26 and the graphics data from a graphics display memory 34. The graphics data are processed and input into graphics display memory 34 by host computer 20 or by a dedicated graphics processor (not shown).

In order to generate three-dimensional images, the CPU 28 can transform a source data volume retrieved from cine memory 16 into an imaging plane data set. In accordance with the preferred embodiments of the invention, the successive transformations involve a composite projection technique. Each pixel in the projected image includes the transformed data derived by projection onto a given image plane.

Figure 3:
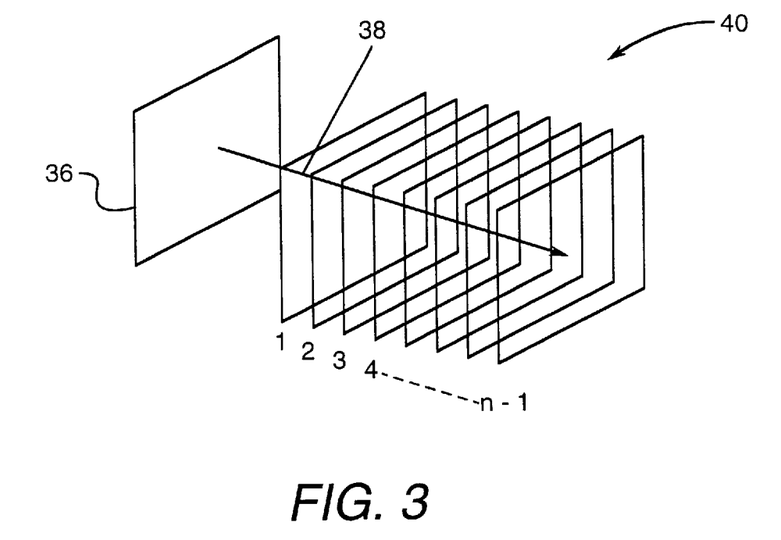
FIG. 3 is a schematic depicting a ray cast through a data volume in accordance with the projection technique of a preferred embodiment of the invention.

A simplified compositing algorithm renders a three-dimensional projection perpendicular to the plane of acquisition. For each pixel in the rendered image 36 (see FIG. 3), a ray 38 is cast through the data volume 40, which comprises n slices numbered from 0 to (n−1). As the ray passes through each plane in the data volume, the contribution to the rendered image of the pixel intersected by the ray is added using the following equation:

$$I_{z,y,x} = I_{z-1,y,x} + O[P_{z,y,x}] \cdot P_{z,y,x}' \cdot O_{r(z,y,x)} \quad (1)$$

where $I_{z,y,x}$ is the accumulated intensity of the projected pixel at (x,y) in plane z; $I_{z-1,y,x}$ is the accumulated intensity of the projected pixel at (x,y) in plane (z−1); $P_{z,y,x}'$ is the depth-shaded intensity of the current (i.e., currently being accumulated) pixel at (x,y) in plane z; $O[P_{z,y,x}]$ is the opacity at (x,y) in plane z (and is a function of the non-depth-shaded pixel intensity); and $O_{r(z,y,x)}$ is the remaining opacity at (x,y) in plane z. The opacity at plane z=0 is equal to unity, i.e., $O_{r(0,y,x)}=1$. At each successive plane z, the remaining opacity is $$O_{r(z,y,x)} = O_{r(z-1,y,x)} \cdot (1 - O[P_{z,y,x}]) \quad (2)$$

The pixels along the ray are summed until the remaining opacity falls below a threshold value.

The opacity function $O[P_{z,y,x}]$ ranges from zero to unity as the pixel value $P_{z,y,x}$ goes from its minimum value to its maximum value.

Figure 4:
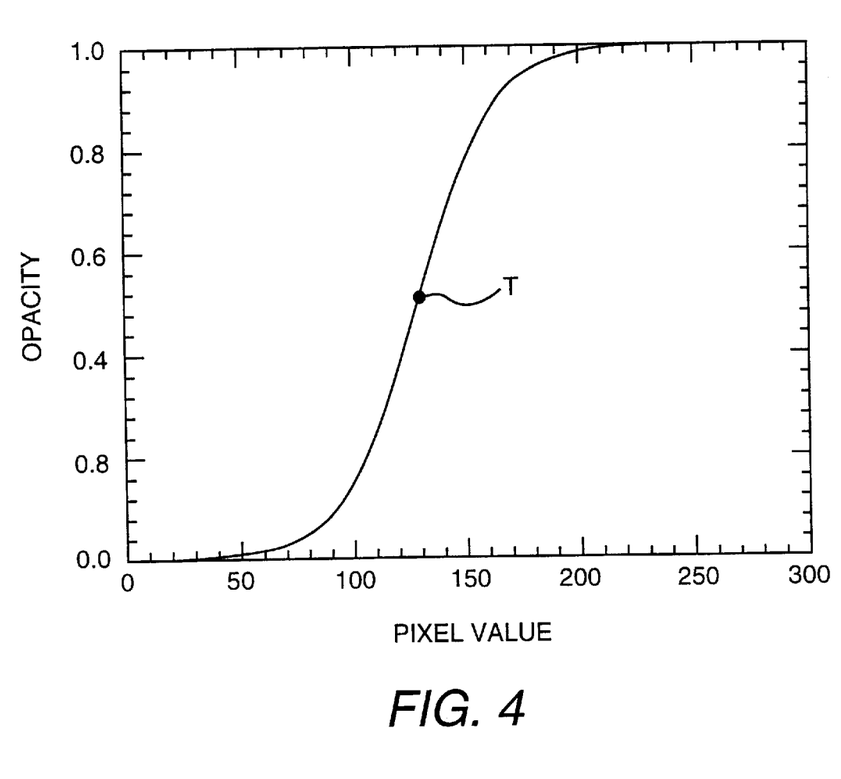
FIG. 4 is a graph of an opacity function of the type employed in a preferred embodiment of the invention.

FIG. 4 shows an opacity curve generated by the function $$O[P_{z,y,x}] = 1 - (1/(\exp((i-T)/W)+1)) \quad (3)$$

where T defines the midpoint of the curve and W defines the slope of the curve. The opacity ranges from 0 to 1.0 as i goes from 0 to 255 (for 8-bit unsigned data). By varying T, one can select the midpoint of pixel intensity values that define the surface of interest. Varying W affects the sharpness of the transition from transparent to opaque and therefore the appearance of the surface.

If the foregoing algorithm were used to re-render the image as the volume is rotated, the intensity of the image would vary because the inter-slice spacing is not taken into account in the opacity function shown in FIG. 2. The opacity as applied to each pixel can be modified to correct for this condition by employing the formula $$O'[P_{z,y,x}] = 1 - (1 - O[P_{z,y,x}])^d \quad (4)$$

where $O[P_{z,y,x}]$ is the original opacity calculated for a given pixel, and d is the inter-slice spacing.

As a further aid to visualization in certain cases, it is desirable (although not required) to create more of an impression of depth. This is done by adding depth shading to the rendering equation as follows:

$$P_{z,y,x}' = \text{MAX}(P_{z,y,x} \cdot (1.0 - i \cdot d \cdot A), 0) \quad (5)$$

where i is the plane number, and A is the amount of attenuation applied at each distance increment d. For example, if the total number of slices were 100 and the amount of attenuation were 10%, then the attenuation for each slice (plane) would be A=0.001. The MAX function ensures the pixel values do not become negative.

A more effective way of eliminating unwanted features in the data volume that obscure anatomy of interest is to interactively remove the feature from the volume by using a pointing device such as a mouse to outline the feature to be removed. This process is sometimes referred to as "electronic scalpeling".

The foregoing surface-enhanced volume rendering technique can be included as one of a panoply of selectable three-dimensional projection techniques employed by an ultrasound imaging system.

Figure 5:
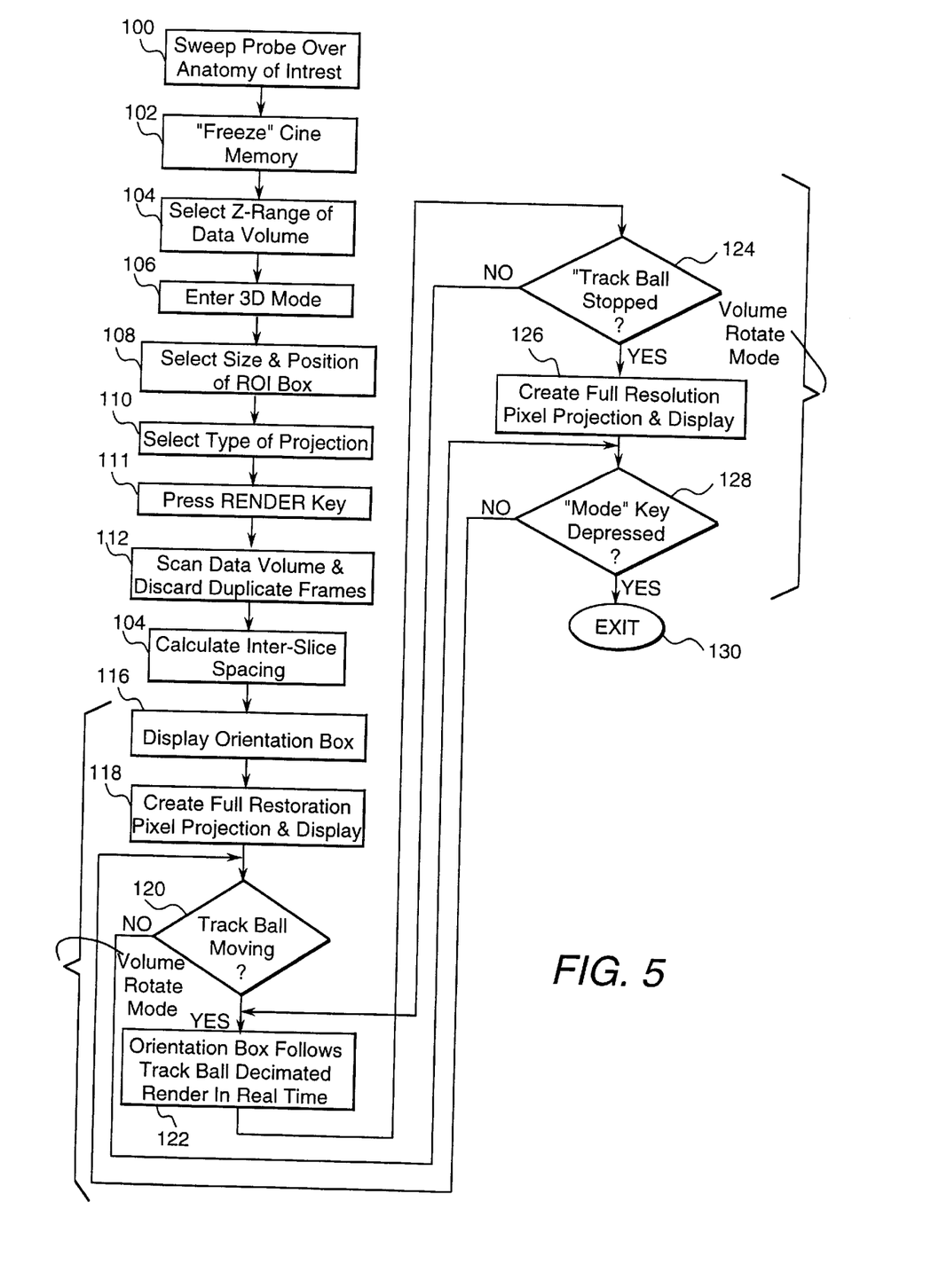
FIG. 5 is a flowchart showing a procedure for acquiring and displaying three-dimensional imaging data.

FIG. 5 is a flowchart showing an image acquisition and display procedure in which the surface-enhanced volume rendering technique in accordance with the preferred embodiment of the invention is included as one of the selectable projection techniques. The user begins by sweeping the ultrasound probe over an area of interest (step 100). For example, the sweep may be acquired by a free-hand sweep in a linear or rocking motion. Once the data are acquired, the user "freezes" the cine memory (step 102) by depressing the Freeze key and then selects the range of cine memory frames (slices) to be included in the Z-dimension of the data volume (step 104). The operator accomplishes the latter step by moving a trackball. A Z-dimension select gauge appears on the display screen when the trackball is moved. The trackball is then used to control the position of an indicator relative to the gauge. The indicator can be moved to a desired left end point and then the left end point is locked by depression of predetermined key on the operator interface. Then the indicator can be moved to a desired right end point and then the right end point is locked by depression of the same predetermined key. This establishes the slices to be included in the data volume. The operator then enters the "3D mode" by depressing the appropriate key on the interface (step 106).

Upon entering the 3D mode, the operator must first select the XY-dimension and location of the ROI (region of interest) within the data volume (step 108). This step is accomplished by manipulating a region of interest box which appears in a default position on the display screen in response to depression of the 3-D mode key. The region of interest box can be sized and translated in X and Y to encompass an imaged structure which appears on a sector scan image. The region of interest box is translated by moving the trackball and is sized by operation of a four-sided rocker switch incorporated in the operator interface.

After the ROI has been defined, the operator selects (step 110 in FIG. 10) the type of three-dimensional projection (minimum, maximum or average pixel projection, surface, the composite technique of the invention, etc.) and the display mode desired, and then presses a render key (step 111). The defined ROI is then retrieved from cine memory 16 (see FIG. 2) by the host computer 20. The host computer scans the retrieved data for duplicate frames and discards them (step 112). The host computer then calculates the inter-slice spacing for the data set (step 114). (The inter-slice spacing is assumed to be constant over the length of the data volume.) For example, the inter-slice spacing can be calculated using the adaptive speckle correlation technique disclosed in U.S. patent application Ser. No. 09/045,780 filed on Mar. 20, 1998 and assigned to the instant assignee.

After calculation of the inter-slice spacing, the system enters a "volume rotate" mode, which is one of three submodes included in the 3D mode. In the "volume rotate" mode, signals representing a colored (e.g., green) orientation box are generated by the host computer (or a dedicated graphics processor), arranged in XY format in the graphics display memory 34 and then sent to the video processor 14. The video processor causes a green orientation box to be displayed on the display screen (step 116). At the same time the host computer performs the selected full-resolution pixel projection of the defined data volume based on the calculated inter-slice spacing (step 118). The projected three-dimensional image is sent to cine memory 16 and then on to video processor 14. Video processor 14 causes the projected three-dimensional image to be displayed on the display screen along with the orientation box. Both the orientation box and the initial projection are oriented with the Z axis pointing into the screen, the Y axis vertical, and the X axis horizontal, i.e., the orientation box appears as a rectangle having X and Y dimensions proportional to the X and Y dimensions of the selected region of interest. The data slices are acquired along the Z axis. This is defined to be the zero angle projection.

In the "volume rotate" mode, the operator can use the trackball to rotate the orientation box and the projected image about the X and Y axes. Rotation about the Z axis is performed using a separate rotary knob on the operator interface. The orientation box and the projected image follow the movement of the trackball and rotary knob in "real-time" so that the user can orient the box as desired. The rotational position of each axis is shown on the display panel. To realize real-time rotation of the projected image, the system detects whether the trackball is moving (step 120). If the trackball is moving, the orientation box follows the trackball and a decimated rendering is performed in real-time (step 122). If the trackball is stopped (step 124), a full-resolution pixel projection is again created and displayed (step 126). If the ultrasound imaging system operator desires to see two-dimensional slices through the data volume at the current X, Y, Z rotation orientation, the operator presses the "display mode" key (step 128 in FIG. 5) to exit (step 130) the "volume rotate" mode and enter the "cut-plane" (reformat) mode (not shown). Techniques for reformatting data to produce arbitrary slices through a data set are well known.

Figure 6:
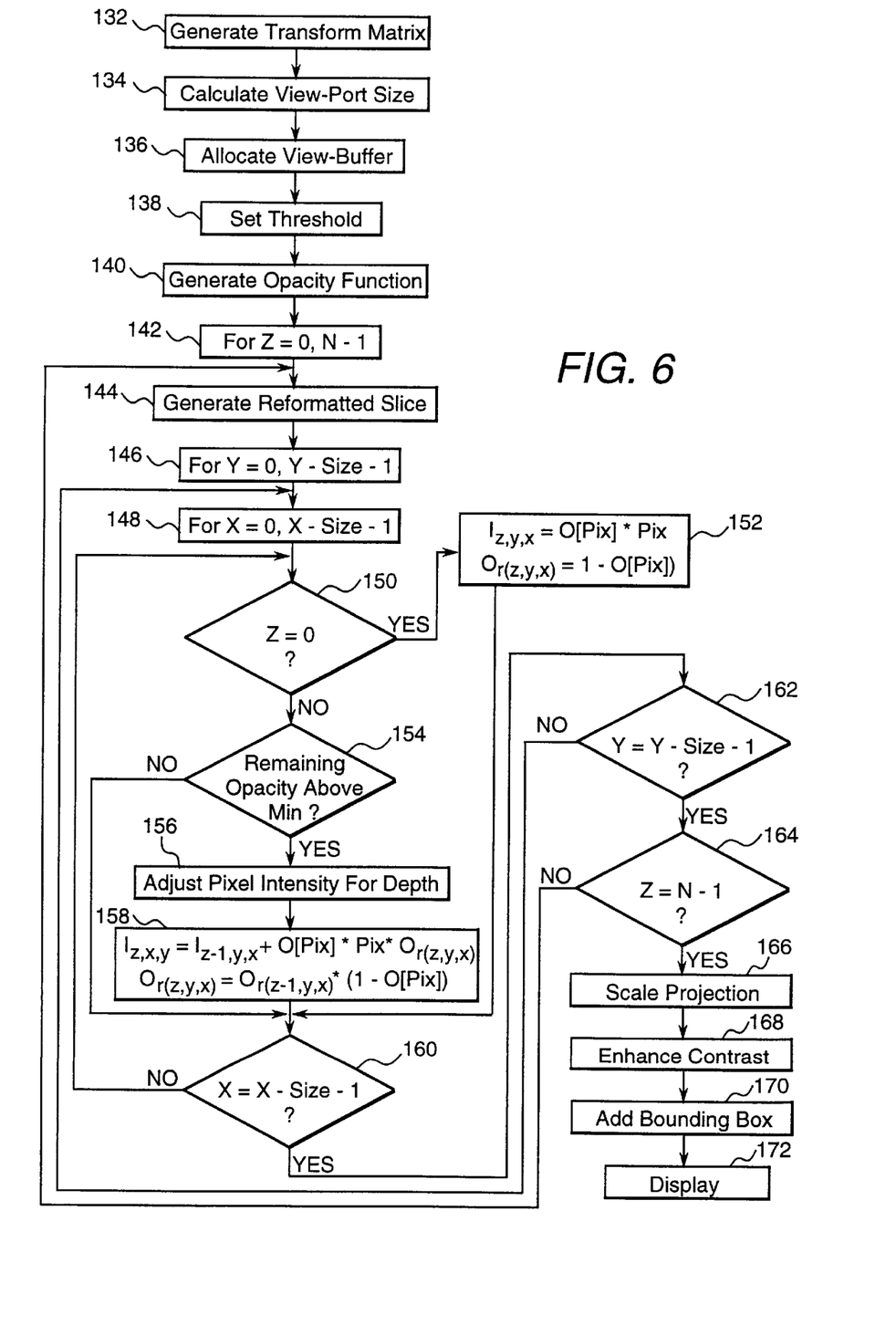
FIG. 6 is a flowchart showing the steps of an algorithm for reconstructing frames comprising successive volumetric projections of pixel data in accordance with the preferred embodiment of the present invention.

In response to selection of the surface-enhanced volume rendering technique (step 110 in FIG. 5) in accordance with a preferred embodiment of the invention, the host computer will create a full-resolution pixel projection (step 118 in FIG. 5) using the procedure generally depicted in FIG. 6. The host computer generates a transformation matrix (step 132) as a function of the angle of rotation of the data volume. The host computer then calculates the dimensions of the memory which will be needed perform the volume rendering operations based on the dimensions of reformatted slices through the rotated data volume (step 134). The host computer allocates a buffer of the required size in system memory (step 136). The operator then sets the threshold T (step 138). In response to this operator input, the host computer generates the opacity function in accordance with Eq. (3) (step 140). For each of n values of z=0 to (n−1) (block 142 in FIG. 6), the host computer then performs the following projection algorithm.

For each value of z, the host computer generates a reformatted slice of data (step 144) which is oriented parallel to the imaging plane. The reformatting is done by taking samples of the pixel values along a respective slice at any angle through the data volume, interpolating between adjacent pixel values as needed. The inter-slice spacing d for the reformatted slices is constrained to be the same as the inter-slice spacing calculated in step 114 of FIG. 5, so that the power d in Eq. (4) is normalized to unity. This allows the system to use the same opacity function for each slice, thereby avoiding the need to generate a new opacity function for each slice in accordance with Eq. (4).

For each reformatted slice, the host computer then calculates the accumulated intensity along rays intersecting pixels on the imaging plane using Eq. (1), the number of slice pixels in the x-direction being x-size and the number of slice pixels in the y direction being y-size, as indicated at steps 146 and 148 in FIG. 6. The variable Pix is successively set equal to each pixel value $P_{z,y,x}$ in the slice being processed, bearing in mind that one need not accumulate the intensities of all pixels in a given slice which are in registration with a respective cast ray, but rather that the x and y incremental steps may vary from slice to slice. If z=0 (step 150), then the accumulated intensity is calculated for each pixel x, y as follows:

$$I_{o,y,x} = O[Pix] \cdot [Pix]$$

(step 152), where Pix=$P_{o,y,x}$. Also the remaining opacity is calculated for each x, y pair as follows:

$$O_{r(0,y,x)} 32\ 1 - O[P_{0,y,x}]$$

These calculations are performed through iterations of x and y from 0 to (x-size−1) and from 0 to (y-size ! 1) respectively (blocks 160 and 162), at which point the routine loops back (since z . . . (n−1)) and generates the next reformatted slice, i.e., for z=1. The host computer again sets the variable Pix equal to each successive pixel value for each x, y pair.

Since z=1, step 152 directs the host computer to determine whether the remaining opacity for each x, y pair in plane z=1 is above a predetermined minimum (step 154). If the remaining opacity is not above the minimum, then the accumulated intensity is not calculated based on that pixel and the algorithm proceeds to the next pixel. If the remaining opacity is above the minimum, then the pixel intensity Pix is adjusted for depth (step 156) in accordance with Eq. (5). Then the accumulated intensity and the remaining opacity are calculated (steps 158) in accordance with Eqs. (1) and (2) respectively. These calculations are performed for all projected pixels in plane z=1. The entire algorithm is then repeated for each successive reformatted slice until the last projected pixel of the last plane z=(n−1) has been processed (step 164). The end result is a set of accumulated pixel intensities for the region of interest being projected onto the imaging plane.

The projection data are then optionally scaled to a larger size (step 166) to counteract the effect of any scaling matrix incorporated in the transformation matrix in order to eliminate holes, i.e., by reducing the distance between any pair of projected pixels in the rotated data volume to 1 unit.

To achieve the best image quality when performing three-dimensional reconstructions of ultrasound images, it is necessary to adjust the contrast of the reconstructed image due to the large variation in the contrast of ultrasound images. Before the projected images are stored in cine memory, the contrast of the pixel intensity data making up those projected images is adjusted (step 168) by the host computer, which creates a one-to-one mapping of unadjusted pixel intensity data into adjusted pixel intensity data. The mapping is generated based on the pixel intensity data of either a source frame or a projected image. In the former case, the mapping is generated before projection; in the latter case, the mapping is generated after projection. The mapping is applied to each projected image to provide contrast adjustment for display.

To generate the contrast adjustment mapping, the host computer compiles a histogram of the number of pixels having an intensity within each of a multiplicity of pre-scribed intensity ranges or bins for one or more slices of source data or for one or more projected images. At the same time, the host computer determines the maximum pixel intensity in the source or projected image. Starting with the bin including the maximum number of pixels and then adding the remaining bins in the order of decreasing number of pixels, the number of pixels in each intensity range or bin are added up until a predetermined percentage of the total number of pixels is reached. When the counted bins include mostly relatively high-intensity pixels, the lower limit of the lowest intensity bin included in the count becomes the pixel intensity threshold. Conversely, when the counted bins include mostly relatively low-intensity pixels, the upper limit of the highest intensity bin included in the count becomes the pixel intensity threshold. In either case, a one-to-one mapping is then created such that the range of intensity values above (or below) the pixel intensity threshold is linearly correlated to an expanded display intensity value range from 0 to 255.

The contrast of each projected image is automatically adjusted, using the mapping generated from the pixel intensity histogram, before the host computer writes that projected image into the cine memory. More specifically, the projected pixel data having intensity values within the range corresponding to the bins included in the histogram count, i.e., within the map input range, are contrast adjusted by transforming each intensity value in the projected pixel data into the corresponding display intensity value established by the one-to-one mapping. The pixel data having intensity values outside the map input range are discarded. By thus increasing the contrast of the pixel intensity data of greatest interest and discarding the pixel intensity data of least interest, each projected image is mapped to the desired brightness and contrast range above or below the pixel threshold depending on the intended result As an aid to visualization, a bounding box is added to the projected image which matches the orientation box (step 170). The projected image and the bounding box are displayed (step 172) with the box overlying the projection. The displayed box is depth shaded to appear to become darker as the box goes towards the "back" of the data volume.

While only certain preferred features of the invention have been illustrated and described, many modifications and changes will occur to those skilled in the art. It is, therefore, to be understood that the appended claims are intended to cover all such modifications and changes as fall within the true spirit of the invention.

What is claimed is:

1. An imaging system comprising:
   a transducer array having a multiplicity of transducer elements for transmitting wave energy in response to electrical activation and transducing returned wave energy into electrical signals;
   a transmitter coupled to said transducer array and programmed to activate a plurality of said transducer elements to transmit focused wave energy for each of a multiplicity of transmit focal positions in each of a multiplicity of scan planes;
   a receiver programmed to form receive signals from electrical signals supplied from said plurality of transducer elements subsequent to each transmit for each of a multiplicity of scan lines in each scan plane;
   a processing subsystem for converting said receive signals into imaging signals for each scan line in each scan plane;
   memory for storing a respective set of imaging signals for each scan plane to form a data volume;
   a computer programmed to perform an algorithm for generating projected image data representing a projection of said data volume onto an imaging plane, wherein said algorithm comprises the steps of:
   (a) generating reformatted slices of pixel data through said data volume, said reformatted slices being mutually parallel; and
   (b) for each of a multiplicity of rays cast from respective pixels on said imaging plane, calculating a respective accumulated intensity for pixels in said reformatted slices which are substantially registered with said respective cast rays to form said projected image data; and
   a subsystem for displaying a projected image which is a function of said projected image data.

2. The system as recited in claim 1, wherein said reformatted slices are substantially parallel to said imaging plane.

3. The system as recited in claim 1, wherein said cast rays are substantially perpendicular to said imaging plane.

4. The system as recited in claim 1, wherein said accumulated intensities are calculated as a function of an opacity function.

5. The system as recited in claim 1, wherein said accumulated intensities along a given cast ray are iteratively calculated for successive reformatted slices in accordance with the equation:

$$I_{z,y,x} = I_{z-1,y,x} + O[P_{z,y,x}] \cdot P_{z,y,x}' \cdot O_{r(z,y,x)}$$

where $I_{z,y,x}$ is the accumulated intensity of the projected pixel at (x,y) in plane z; $I_{z-1,y,x}$ is the accumulated intensity of the projected pixel at (x,y) in plane (z–1); $P_{z,y,x}'$ is the depth-shaded intensity of the current (i.e., currently being accumulated) pixel at (x,y) in plane z; $O[P_{z,y,x}]$ is the opacity at (x,y) in plane z (and is a function of the non-depth-shaded pixel intensity); and $O_{r(z,y,x)}$ is the remaining opacity at (x,y) in plane z.

6. The system as recited in claim 5, wherein the remaining opacity is calculated for successive reformatted slices in accordance with the equation:

$$O_{r(z,y,x)} = O_{r(z-1,y,x)} \cdot (1 - O[P_{z,y,x}]).$$

7. The system as recited in claim 5, wherein the Pix values are calculated as a function of a product of an attenuation factor and a slice number.

8. The system as recited in claim 7, wherein the $P_{z,y,x}'$ values are calculated in accordance with the equation:

$$P_{z,y,x}' = \text{MAX}(P_{z,y,x} \cdot (1.0 - i \cdot d \cdot A), 0)$$

wherein $P_{z,y,x}$ is the intensity of the pixel at (x,y) in plane z without depth shading; i is the slice number; and A is the amount of attenuation applied at each distance increment d.

9. An imaging system comprising:
   a transducer array having a multiplicity of transducer elements for transmitting wave energy in response to electrical activation and transducing returned wave energy into electrical signals;
   a display monitor for displaying an image; and
   a computer programmed to perform the following steps:
   (a) activating transducer elements of said array to transmit focused wave energy for each of a multiplicity of transmit focal positions in each of a multiplicity of scan planes;
   (b) forming receive signals from electrical signals supplied from said plurality of transducer elements subsequent to each transmit for each of a multiplicity of scan lines in each scan plane;
   (c) converting said receive signals into imaging signals for each scan line in each scan plane;
   (d) storing a respective set of imaging signals for each scan plane to form a data volume;
   (e) generating reformatted slices of pixel data through said data volume, said reformatted slices being mutually parallel;

(f) for each of a multiplicity of rays cast from respective pixels on said imaging plane, calculating a respective accumulated intensity for pixels in said reformatted slices which are substantially registered with said respective cast rays to form projected image data representing a three-dimensional image; and (g) sending said projected image data to said display monitor.

10. The system as recited in claim 9, wherein said reformatted slices are substantially parallel to said imaging plane.

11. The system as recited in claim 9, wherein said cast rays are substantially perpendicular to said imaging plane.

12. A method for three-dimensional imaging of a volume of matter, comprising the steps of:

transmitting focused wave energy for each of a multiplicity of transmit focal positions in each of a multiplicity of scan planes intersecting the volume of matter;

generating echo signals derived from echoes of wave energy returned from the volume of matter following each transmit for each of a multiplicity of scan lines in each scan plane;

converting said receive signals into imaging signals for each scan line in each scan plane;

storing a respective set of imaging signals for each scan plane to form a data volume;

generating reformatted slices of pixel data through said data volume, said reformatted slices being mutually parallel;

for each of a multiplicity of rays cast from respective pixels on said imaging plane, calculating a respective accumulated intensity for pixels in said reformatted slices which are substantially registered with said respective cast rays to form projected image data; and displaying a three-dimensional image which is a function of said projected image data.

13. The method as recited in claim 12, wherein said reformatted slices are substantially parallel to said imaging plane.

14. The method as recited in claim 12, wherein said cast rays are substantially perpendicular to said imaging plane.

15. The method as recited in claim 12, wherein said accumulated intensities are calculated as a function of an opacity function.

16. The method as recited in claim 12, wherein said accumulated intensities along a given cast ray are iteratively calculated for successive reformatted slices in accordance with the equation:

$$I_{z,y,x} = I_{z-1,y,x} + O[P_{z,y,x}] \cdot P_{z,y,x}' \cdot O_{r(z,y,x)}$$

where $I_{z,y,x}$ is the accumulated intensity of the projected pixel at (x,y) in plane z; $I_{z-1,y,x}$ is the accumulated intensity of the projected pixel at (x,y) in plane (z-1); $P_{z,y,x}'$ is the depth-shaded intensity of the current (i.e., currently being accumulated) pixel at (x,y) in plane z; $O[P_{z,y,x}]$ is the opacity at (x,y) in plane z (and is a function of the non-depth-shaded pixel intensity); and $O_{r(z,y,x)}$ is the remaining opacity at (x,y) in plane z.

17. The method as recited in claim 16, wherein the remaining opacity is calculated for successive reformatted slices in accordance with the equation:

$$O_{r(z,y,x)} = O_{r(z-1,y,x)} \cdot (1 - O[P_{z,y,x}]).$$

18. The method as recited in claim 16, wherein the Pix values are calculated as a function of a product of an attenuation factor and a slice number.

19. The method as recited in claim 18, wherein the $P_{z,y,x}'$ values are calculated in accordance with the equation:

$$P_{z,y,x}' = \text{MAX}(P_{z,y,x} \cdot (1.0 - i \cdot d \cdot A), 0)$$

wherein $P_{z,y,x}$ is the intensity of the pixel at (x,y) in plane z without depth shading; i is the slice number; and A is the amount of attenuation applied at each distance increment d.

20. A system for three-dimensional imaging of a volume of matter, comprising:

a transducer array having a multiplicity of transducer elements for transmitting wave energy in response to electrical activation and transducing returned wave energy into electrical signals;

means for activating a plurality of said transducer elements to transmit focused wave energy for each of a multiplicity of transmit focal positions in each of a multiplicity of scan planes;

means for forming receive signals from electrical signals supplied from said plurality of transducer elements subsequent to each transmit for each of a multiplicity of scan lines in each scan plane;

means for converting said receive signals into imaging signals for each scan line in each scan plane;

memory for storing a respective set of imaging signals for each scan plane to form a data volume;

means for generating reformatted slices of pixel data through said data volume, said reformatted slices being mutually parallel;

means for calculating a respective accumulated intensity for pixels in said reformatted slices which are substantially registered with a respective cast ray for each of a multiplicity of rays cast from respective pixels on said imaging plane, said accumulated pixel intensities forming projected image data; and means for displaying a three-dimensional image which is a function of said projected image data.

* * * * *